US010076672B2

United States Patent
Grant

(10) Patent No.: US 10,076,672 B2
(45) Date of Patent: Sep. 18, 2018

(54) METHODS FOR EMPLOYING DIGITAL ROOT TECHNIQUES TO GENERATE COMPUTER-INPUT DATA

(71) Applicant: STRATHSPEY CROWN HOLDINGS, LLC, Newport Beach, CA (US)

(72) Inventor: Robert Edward Grant, Laguna Beach, CA (US)

(73) Assignee: Strathspey Crown Holdings, LLC, Newport Beach, CA (US)

( * ) Notice: Subject to any disclaimer, the term of this patent is extended or adjusted under 35 U.S.C. 154(b) by 355 days.

(21) Appl. No.: 14/946,605

(22) Filed: Nov. 19, 2015

(65) Prior Publication Data
US 2017/0143992 A1    May 25, 2017

(51) Int. Cl.
*A61N 5/00* (2006.01)
*A61N 5/10* (2006.01)
*A61N 5/06* (2006.01)

(52) U.S. Cl.
CPC .............. *A61N 5/103* (2013.01); *A61N 5/06* (2013.01)

(58) Field of Classification Search
CPC ........ A61N 5/06; A61N 5/103; A61N 5/1031; A61N 5/1048
USPC ........................................................ 600/1–8
See application file for complete search history.

*Primary Examiner* — John Lacyk
(74) *Attorney, Agent, or Firm* — Fish IP Law, LLP

(57) ABSTRACT

A methodology in accordance with the present invention is directed toward optimizing the operational parameters of a radiation unit which will be used in a protocol to influence a target tissue (cellular structure), in a predetermined manner. Specifically, digital root techniques are used for this purpose. To do this, the digital root is determined for a number that is characteristic of a cellular structure attribute that is to be influenced by radiation. This digital root is then expanded into the range of a selected operational parameter for the radiation unit. Thus, a number in the operational range of the radiation unit is selected to establish an appropriate radiation parameter for influencing the cellular structure.

7 Claims, 2 Drawing Sheets

METHODS FOR EMPLOYING DIGITAL ROOT TECHNIQUES TO GENERATE COMPUTER-INPUT DATA

FIELD OF THE INVENTION

The present invention pertains generally to systems and methods for incorporating informational numbers into a set-up operation for implementing a radiation therapy. More particularly, the present invention pertains to the manipulation of numbers for the purpose of establishing operational parameters which can be used by a radiation unit to perform a protocol that will influence cellular structure in a target tissue of a patient. The present invention is particularly, but not exclusively, useful for employing digital root technology to define a radiation strategy for influencing cellular structure in a patient.

BACKGROUND OF THE INVENTION

As a mathematical definition, a number is a symbol or a group of symbols showing how many of something there are, or at what place something may be in a sequence. As a practical matter, however, a number can mean much more. Indeed, to name but a few of their attributes, numbers convey information that describe, differentiate, evaluate, predict, quantify, justify and regulate much of what we do in our everyday lives. In sum, all measurements are based on numbers.

Numbers do not exist in isolation, without any meaning. They always require context. Moreover, comparisons between different numbers often add meaning to a particular circumstance that, without context, would otherwise be nonsensical (e.g. weight and balance calculations for a flyable aircraft, or stock market trends). Further, it has happened that numbers for many circumstances have become so extremely complex, and numbers often have such orders of magnitude, that the number becomes essentially incomprehensible (e.g. the national debt).

Nevertheless, despite the above observations, numbers remain an essential means for transferring information. For example, consider health and wellness issues which are presently being confronted in the field of medicine. Pharmaceutical preparations for instance result from clinical studies wherein numbers provide very important information about the safety and efficacy of a particular preparation. Likewise, the evaluation of medical devices and surgical protocols require number comparisons. Clinical considerations for the health and wellness of a patient are now, however, looking beyond the more traditional techniques. Still, and perhaps more so, numbers are important.

Of particular interest here is the use of radiation treatments for curing health and wellness issues. In this context, radiations throughout the electromagnetic spectrum are of general interest. More particularly, sonic radiation as disclosed in U.S. patent application Ser. No. 14/488,101 filed on Sep. 16, 2014, and electromagnetic radiation as disclosed in U.S. patent application Ser. No. 14/632,941 filed on Feb. 26, 2015, are considered for purposes of the present invention. For these considerations, physical characteristics of the radiation's operational parameters must be established (e.g. wavelength $\lambda$, intensity, pulse duration, fluence, optics, and variations of these). Similarly, physical characteristics of the tissue that is to be radiated must also be identified (e.g. tissue volume, practical dimensions, tissue type, fundamental frequencies, cellular structure, abnormalities, and various combinations of these). It happens that all of the operational parameters and tissue characteristics can each be somehow identified by a number. The respective numbers, however, can be lengthy and be either very large or extremely small. Moreover, they may be different from each other by many orders of magnitude. Despite such disparities, however, for operational purposes the numbers may need to be congruent.

With the above in mind, the present invention recognizes that in almost any circumstance, an operation can be described by selecting appropriate numbers. Furthermore, the present invention recognizes that numbers can be selected which will cooperatively interact with each other to achieve a purpose. As noted above, however, and depending on the particular operation of interest, the selected numbers may have many digits, be cumbersome and difficult to manipulate. In such situations, it is desirable if the numbers can somehow be simplified.

There are several numerology techniques that are familiar for associating and manipulating numbers with other numbers. Of these, digital root techniques appear promising insofar as manipulating lengthy numbers, with significantly different orders of magnitude, is concerned. Importantly, digital root techniques can be computer-implemented. In overview, a digital root, dr, is a non-negative integer that is obtained by an iterative process of summing digits.

For a brief discussion of digital root techniques, consider the number 7,851,437 whose digital root, dr, is 8. Because:

$7+8+5+1+4+3+7=35$; and $3+5=8$

Similarly, the number 92,546 also has the digital root 8. Because:

$9+2+5+4+6=26$; and $2+6=8$

The import here is the number 8 is easier to deal with than either 7,851,437 or 92,546. Moreover, there is congruency, which establishes a unique relationship between the various numbers. As a step further in this process, it is also known that the products obtained when digital roots are multiplied together can be arranged in a so called "Vedic square" which illustrates other relationships between numbers.

In light of the above, it is an object of the present invention to provide a method for setting a protocol which uses radiation to influence a cellular structure in a tissue wherein an operable cooperation between the radiation and the cellular structure of the tissue is achieved by evaluating numerical attributes of both. Another object of the present invention is to set a protocol for a radiation unit which employs operational parameters for the radiation unit that are congruent with physical attributes of the target tissue. Still another object of the present invention is to provide a system and method for influencing the health and wellness of a patient that is easy to implement, is simple to operate and is comparatively cost effective.

SUMMARY OF THE INVENTION

As used here, a small letter, n, is a number that is characteristic of a physical attribute of a cellular structure. For a plurality of different attributes, the letter m is used to identify an m number of different attributes, where m is a number from 1 to m. Thus, each individual attribute can be designated $n_m$. Similarly, as used here, a capital letter N is a number which characterizes the magnitude of an operational parameter for the radiation device that is used to implement a protocol affecting a particular cellular structure. It is envisioned there will be a p number of operational parameters required for the radiation device, where p is a number from 1 to p. Thus, each operational parameter can be designated $N_p$.

A preferred embodiment of the present invention envisions an operational protocol wherein it is first necessary to determine the digital root $dr_{(nm)}$ of a selected number n that is characteristic of a cellular structure. As indicated above, for purposes of the present invention, this selected number $dr_{(nm)}$ will represent the characteristic (attribute) of the m number cellular structure. Typically, the selected number will be based on cellular attributes such as cell type, resonant frequency, size, chemical structure, anatomical structure, atomic number, and atomic weight. Further, the selected number n can be obtained from look-up tables, data banks, and/or clinical evaluations. In any event, a digital root $dr_{(nm)}$ will be calculated for the selected number (i.e. cellular attribute).

The digital root $dr_{(nm)}$ that is calculated for the cellular structure is then used as the digital root $dr_{(Np)}$ for a number $N_p$ that is representative of a predetermined operational parameter of the radiation unit (i.e. $dr_{(nm)} = dr_{(Np)}$). The digital root $dr_{(Np)}$ is then expanded into a range for selection of the operational parameter of the radiation unit that is to be used for influencing the cellular structure. For example, operational parameters of interest will typically include wavelength (λ), intensity (I), pulse duration, focal spot size, scan rate, fluence and phase. Further, each operational parameter $N_p$ will be appropriately selected based on considerations of frequency range, harmonic interactions and other numerical relationships.

The above process can then be repeated as necessary, for a plurality of cellular structure characteristics $dr_{(nm)}$, and for a plurality of radiation unit parameters $dr_{(Np)}$. Once the operational parameter(s) is (are) identified for the operation of the radiation unit, the protocol can be performed on the cellular structure.

For an alternate embodiment of the present invention, the digital root of the cellular structure $dr_{(nm)}$ and the digital root of an operational parameter $dr_{(Np)}$ are calculated independently. The digital roots $dr_{(nm)}$ and $dr_{(Np)}$ are then compared with each other. If they are equal, i.e. $dr_{(nm)} = dr_{(Np)}$, then the operational parameter number $N_p$ is used for the protocol. Otherwise, $dr_{(Np)}$ is appropriately incremented or decremented until $dr_{(Np)}$ is equal to $dr_{(nm)}$. Thus, in the alternate embodiment, $N_p$ is determined slightly differently, but it is still implemented as disclosed above for the preferred embodiment.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
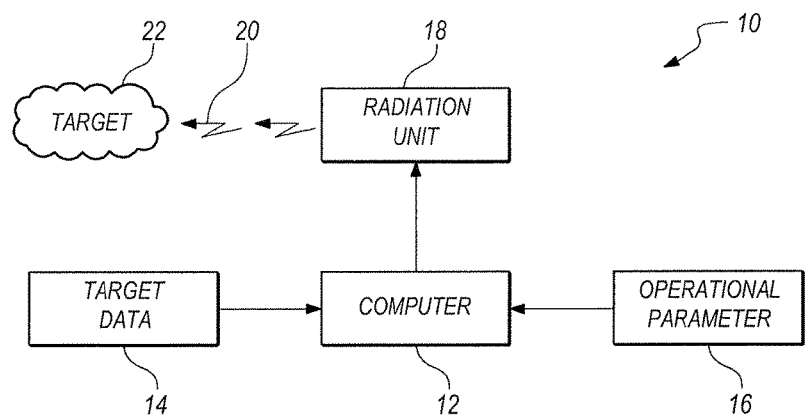
FIG. 1 is a functional schematic of the interactive components that are involved in setting up a protocol in accordance with the present invention.

Referring initially to FIG. 1 a system in accordance with the present invention is shown and is generally designated 10. As shown, the system 10 includes a computer 12 that receives target data 14 and operational parameters 16 as input. Further, FIG. 1 shows that the output of computer 12 is directed to a radiation unit 18. In turn, it is shown that the radiation unit 18 generates a radiation beam 20 that is directed onto target tissue 22.

It is an important concept of the present invention that both the target data 14 and the operational parameters 16 can both be represented by characteristic numbers. Specifically, it is to be appreciated that the target data 14 will include various cellular structures of the target tissue 22 (not specifically shown) which will each have attributes that can be associated with a respective number. Thus, each attribute can be characterized by a number n. For instance, attributes of a cellular structure, such as cell type, resonant frequency, size, chemical structure, anatomical structure, atomic number and atomic weight can each be associated with a number.

Similarly, the operational parameters 16 will include various characteristics of the radiation beam 20 that will be established to influence a cellular structure in the target tissue 22. For example, such characteristics typically include such factors as wavelength (λ), intensity (I), pulse duration, focal spot size, scan rate, fluence and phase. In this case, each operational parameter will be represented by a number N.

As recognized for the present invention, a number n and a number N will respectively determine how the radiation beam 20 will affect a cellular structure in the target tissue 22. For purposes of the present invention it is recognized that n and N should be congruent. In particular, with congruence in mind, the present invention uses the manipulation of numbers by digital root techniques to thereby establish an operational interaction between characteristics of the radiation beam 20 (i.e. operational parameters 16) and attributes of cellular structure target tissue 22 (i.e. target data 14). Depending on the particular application, the objective is to somehow influence cellular structure within the target tissue 22 with the radiation beam 20.

Figure 2:
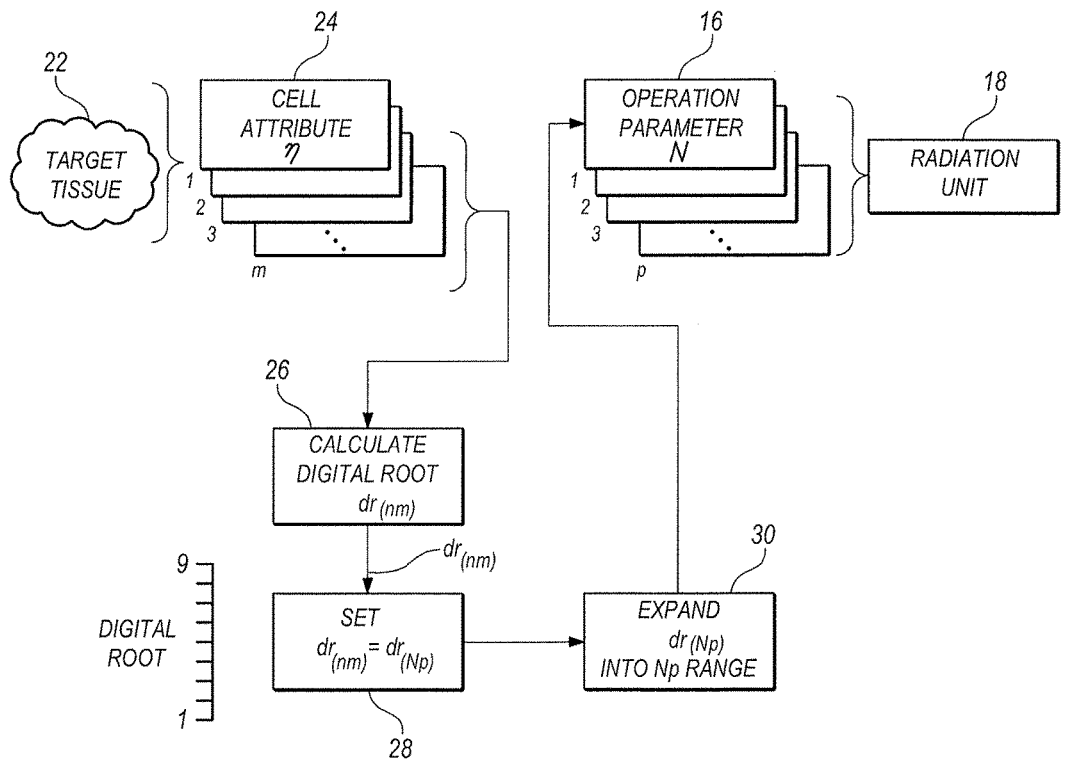
FIG. 2 is a logic flow chart of the interactive tasks and data flow required for a preferred embodiment of the present invention.
Figure 3:
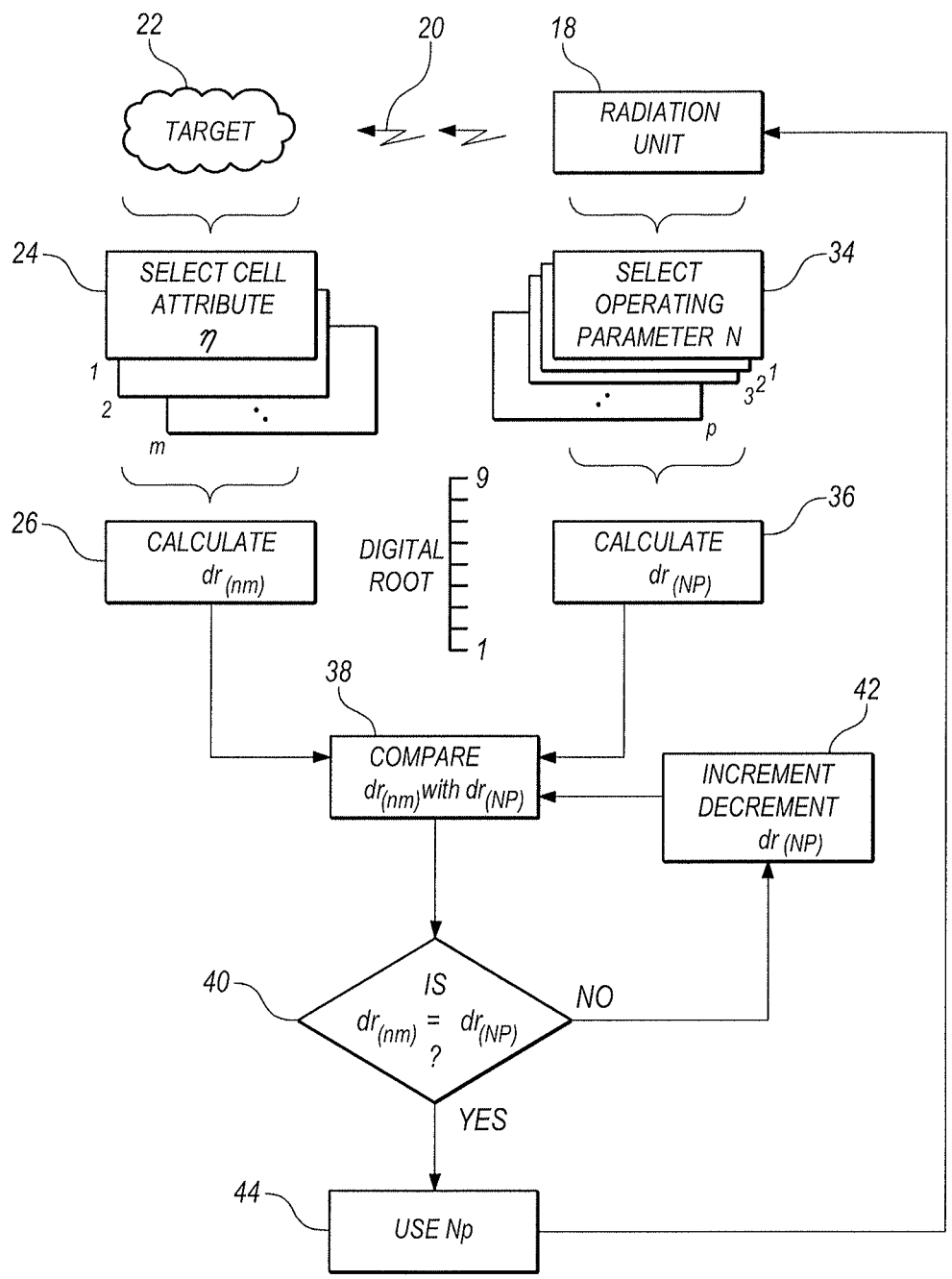
FIG. 3 is a logic flow chart of the interactive tasks and data flow required for an alternate embodiment of the present invention.

For an operation of the present invention, digital root techniques can be manipulated in either of two ways. One way (a first embodiment), is shown in FIG. 2. Another way (a second embodiment) is shown in FIG. 3.

As shown in FIG. 2, the first embodiment requires selecting attributes of interest for the cellular structure in target tissue 22. The target data 14 is then based on these selections. Each selected attribute (i.e. target data 14) is then represented by a number n [see block(s) 24 in FIG. 2]. As indicated above, if an m number of attributes are selected, numbers $n_m$ are to be considered, where m is an integer from 1 to m.

Once the numbers $n_m$ are determined, their digital roots $dr_{(nm)}$ are then individually calculated [see block 26 in FIG. 2]. Note: at this point, the number N for operational parameters 16 of the radiation beam 20 has (have) not yet been determined. Also, if there are a p number of undetermined operational characteristics for the radiation beam 20, where p is an integer from 1 to p, the various numbers $N_p$ still need to be determined.

In accordance with the first embodiment of the present invention (FIG. 2), although $N_p$ is still not known after $dr_{(nm)}$ has been calculated, an operational range for a particular operational parameter 16 of the radiation beam 20 is known. Therefore, to be congruent with $n_m$, the digital root of a number $N_p$, $dr_{(Np)}$, which is representative of an operational parameter 16, can be considered to be equal to the digital root $dr_{(nm)}$ of a selected attribute of a cellular structure in the target tissue 22 (i.e. $dr_{(nm)} = dr_{(Np)}$) [see block 28 in FIG. 2].

Consequently, $dr_{(nm)}$ (i.e. $dr_{(Np)}$ can be expanded into the known operational range of an operational parameter 16 [see block 30]. An appropriate number $N_p$ can then be selected from the operational range which is representative of an operational parameter 16 of the radiation beam 20.

For the second embodiment of the present invention, shown in FIG. 3, the digital roots $dr_{(nm)}$ for selected attributes of the cellular structure in target tissue 22 are calculated, in a manner similar to that disclosed above for the first embodiment [see blocks 24 and 26 in FIGS. 2 and 3]. For the second embodiment, however, after a digital root $dr_{(nm)}$ has been calculated, a number $N_p$ is selected from within the operational range of the particular operational parameter 16 of interest [see block 34]. The digital root $dr_{(Np)}$ for the selected $N_p$ is then calculated [see block 36]. Next, $dr_{(Np)}$ is compared with the corresponding $dr_{(nm)}$ [see block 38].

Based on the comparison of $dr_{(nm)}$ with $dr_{(Np)}$ [block 38], a determination is made as to whether they are equal (i.e. is $dr_{(nm)} = dr_{(Np)}$ [see inquiry block 40]. If they are not equal, $dr_{(Np)}$ is incremented or decremented until $dr_{(nm)} = dr_{(Np)}$ [see block 42]. The digital root $dr_{(Np)}$ is then used for the number $N_p$ [see Block 44].

While the particular Methods for Employing Digital Root Techniques to Generate Computer-Input Data as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for establishing a radiation protocol to influence cellular structure in a tissue, the method comprising the steps of:

identifying a target tissue;

choosing a cellular structure in the target tissue to be influenced; attributing a number, n, to the cellular structure chosen during the choosing step, wherein n is characteristic of a physical attribute of the cellular structure;

repeating the attributing step an m number of times to attribute a number nm for each of m different attributes of the cellular structure, wherein m is a number from 1 to m;

calculating a digital root, dr(nm), for each nm;

conforming a digital root dr(nm) selected from the calculating step with a digital root dr(np) of a number Np, wherein the magnitude of the number Np is characteristic of an operational parameter for a radiation unit, wherein Np is within the operational range of the radiation unit and there are a p number of operational parameters, and further wherein p is a number from 1 to p;

determining an optimal congruence based on the conforming step for each combination of nm and Np; and operating the radiation unit with the Np of the determining step to influence cellular structure of the tissue.

2. The method of claim 1 wherein the conforming step comprises the steps of:

setting the digital root for each Np, dr(Np), equal to the digital dr(nmJ obtained during the calculating step; and expanding d(nm) into the operational range for Np.

3. The method of claim 1 wherein the conforming step comprises the steps of:

comparing dr(Np) with dr(nm);

incrementing/decrementing dr(Np) until dr(Np) equals dr(nm); and selecting an Np for operation of the radiation unit, wherein a selection of Np is based on dr(Np) being set equal to drnmJ of the chosen cellular structure dr(nm) =dr(Np).

4. The method of claim 1 further comprising the step of weighting each number nm according to its susceptibility for influence by a radiation.

5. The method of claim 1 further comprising the step of varying Np within its operational range.

6. The method of claim 1 further comprising the step of selecting nm from the group consisting of cell type, resonant frequency, size, chemical structure, anatomical structure, atomic number and atomic weight.

7. The method of claim 1 further comprising the step of selecting Np from the group consisting of wavelength (λ), intensity (I), pulse duration, focal spot size, scan rate, fluence and phase.

* * * * *